ed. at 222 (Thomas 1966).

United States Patent [19]
Prodell

[11] 4,282,002
[45] Aug. 4, 1981

[54] SENSITIZED SHEEP STROMA IMMUNOASSAY FOR RHEUMATOID FACTOR

[75] Inventor: Rita C. Prodell, West Orange, N.J.

[73] Assignee: Akzona Incorporated, Asheville, N.C.

[21] Appl. No.: 73,167

[22] Filed: Sep. 6, 1979

[51] Int. Cl.³ .......................................... G01N 33/54
[52] U.S. Cl. .................................. 23/230 B; 23/915; 422/56; 424/12
[58] Field of Search ................ 23/230 B, 915; 424/12; 422/56, 61

[56] References Cited

U.S. PATENT DOCUMENTS

| | | | |
|---|---|---|---|
| 3,548,051 | 12/1970 | Dingwall | 424/3 |
| 3,565,987 | 2/1971 | Schuurs | 424/12 |
| 3,594,466 | 7/1971 | Guffroy | 424/12 |
| 3,654,083 | 4/1972 | Schuurs | 195/63 |
| 3,655,838 | 4/1972 | Price et al. | 264/13 |
| 3,655,874 | 4/1972 | van Hell | 424/99 |
| 3,666,421 | 5/1972 | Price | 23/253 TP |
| 3,689,632 | 9/1972 | Mizushima et al. | 424/12 |
| 3,714,344 | 1/1973 | Brown | 424/1 |
| 3,714,345 | 1/1973 | Hirata | 424/3 |
| 3,826,613 | 12/1973 | Huber | 424/12 |
| 3,843,777 | 7/1974 | Parikh et al. | 23/230 B |
| 3,862,302 | 1/1975 | Price et al. | 424/12 |
| 3,899,298 | 8/1975 | Szczesniak | 23/253 R |
| 3,903,254 | 9/1975 | Dahlgren et al. | 424/12 |
| 3,905,767 | 9/1975 | Morris et al. | 23/230 B |
| 4,053,284 | 10/1977 | Posch | 23/259 |
| 4,055,394 | 10/1977 | Friedmann et al. | 23/253 TP |
| 4,062,935 | 12/1975 | Masson et al. | 424/12 |

OTHER PUBLICATIONS

Hepler, Manual of Clinical Laboratory Methods, 4th ed. at 222 (Thomas 1966).
Singer and Plotz, "The Latex Fixation Test", American J. of Med. 21 at 888-892 (1956).
Bartfield, "Distribution of Rheumatoid Factor Activity in Non-rheumatoid States", Annals, New York Academy of Sciences at 30-40 (1970 (?)).
I. Davidson, "Serologic Diagnosis of Infectious Mononucleosis", J. Amer. Med. Asso. 108(4) at 289-295 (1937).
Waaler, "On the Occurrence of a Factor in Human Serum Activating the Specific Agglutination of Sheep Blood Corpuscles", Acta Path. Micro Biol. Scand. 17 at 172-188 (1940).
Rose et al., Proc. Soc. Exp. Biol. Med. 68 at 1 et seq (1948).
Heller, et al., "The Hemaaglutination Test for Rheumatoid Arthritis", Part II, J. Immun. 72 at 66-78 (1954) and Id, Pt. I, J. Immun. 69 at 27-40 (1952).
E. Engvall & P. Perlmann, "Enzyme-linked Immunosorbent Assay, Elisa", J. Immunology 109(1) at 129-135 (1972).
John S. Cowdery et al., "A Radioimmunoassay for Human Antigen-Antibody Complexes in Clinical Material", J. Immunology 114(1) at 5-9 (1975).

*Primary Examiner*—Arnold Turk
*Attorney, Agent, or Firm*—Robert H. Falk; Wayne W. Herrington; Francis W. Young

[57] ABSTRACT

A new and immunochemically useful reagent is disclosed for the detection of rheumatoid factors (RF) in human blood, plasma, serum or synovial fluid in agglutination reactions, together with a new clinical diagnostic test and test slide using said reagent. The reagent consists essentially of a supply of red cell stroma having absorbed upon their surface a sensitizing agent. Preferably the red cell stroma is sheep red cell stroma, and most preferably the sensitizing agent is rabbit anti-sheep red cell globulin.

24 Claims, No Drawings

SENSITIZED SHEEP STROMA IMMUNOASSAY FOR RHEUMATOID FACTOR

BACKGROUND OF THE INVENTION

1. Field of the Invention

This invention relates to a new immunochemical reagent, a new clinical diagnostic test using such reagent, and a test slide using such reagent. More particularly, the invention relates to a new carrier on which globulins useful in clinical diagnostic agglutination reactions may be permanently fixed. The new reagent is particularly useful in agglutination reactions for the detection of rheumatoid factors (RF), and may be advantageously dried onto a test slide to which a test solution may be later applied.

2. Description of the Prior Art

Serologic agglutination reactions have long formed the basis of tests useful in the clinical diagnosis of disease, particularly of bacterial, parasitic, rickssettial and viral diseases. Some of these tests are relatively simple, others require special facilities. Many of the serologic agglutination tests useful today are described in Davidsohn and Wells, *Clinical Diagnosis by Laboratory Methods,* 13th ed., chaps. 23-24 (Saunders: Philadelphia 1962).

Among the many diseases which may be diagnosed by a serological agglutination test is rheumatoid arthritis. In the serum of the majority of patients having this disease, there exist certain factors—termed rheumatoid factors (RF)—which react in a variety of serologic systems, all of which contain gamma globulin in some form. The exact nature of RF is not certain. Evidence points to their being anti-bodies with specificity for gamma globulin, particularly immunoglobulin G, and certainly they behave as if they were such in serological agglutination reactions.

The agglutinating capacity of RF was first noted in 1940 by Waaler who reported (Acta Path. Microbiol. Scand. 17:172, 1949) on the agglutination of sensitized sheep cells (sheep erthrocytes "coated" with rabbit anti-sheep cell anti-bodies) by rheumatoid arthritis sera. In 1948, this phenomenon was rediscovered by Rose and others and proposed (Proc. Soc. Exp. Biol. Med. 68:1, 1948) as the basis for the diagnostic test known as SCAT—sheep cell agglutination test. This test has since been greatly improved and modified. In 1954, Heller and co-workers demonstrated the reactivity of RF for human gamma globulins when they discovered that Fraction II (FII) human gamma globulin could inhibit the agglutinating property of rheumatoid sera in the SCAT and that tanned sheep cells "coated" with FII human gamma globulin were agglutinated by rheumatoid sera. (J. Immun. 72:66, 1954 and 69:27, 1952). This work was followed by the fashioning of numerous agglutination tests for RF in which red cells or inert particles were coated with antibody or gamma globulin which could then be exposed to and agglutinated by serum containing RF. These tests are referred to at pages 891-894 of *Clinical Diagnosis by Laboratory Methods,* referred to above, and also in articles by Christian, "Rheumatoid Factors A. Nature and Significance of Rheumatoid Factors" and Cathcart, "Rheumatoid Factors B. Serologic Techniques", both in the treatise *Laboratory Diagnostic Procedures in Rheumatic Diseases* (Little, Brown and Co., Boston, 1967).

The "perfect" diagnostic test for rheumatoid arthritis has yet to be discovered—one which will be completely specific for that disorder, yet sensitive enough to detect every patient who has definite disease. The most specific serologic tests are those which employ rabbit gamma globulin, such as the SCAT test referred to above. However, these are not as sensitive as tests employing human gamma globulin, such as the FII latex fixation test in which FII human gamma globulin is coated on latex particles. (The latter test is described in the references above and was originally described by Singer and Plotz in the American Journal of Medicine, Vol. 21, p. 888 (1956).) The SCAT has other drawbacks as well. It requires fresh sheep blood cells collected in Alsever's Solution; these cells are stable only for a period of about two weeks and must be washed and brought to a 2%, by volume, suspension for sensitizing with the rabbit anti-sheep red cell antiserum (amboceptor). As the cells age, the amount of amboceptor necessary to achieve a given level of sensitivity may vary. Once sensitized, the cells must be used immediately. These disadvantages have caused the SCAT to become less popular than tests using inert particles instead of red cells on which to coat the antibody or gamma globulin, even though, as mentioned above, the SCAT is the most specific serological test known for rheumatoid arthritis. This lessening in popularity has been aggravated by the fact that it is not possible to use the SCAT in a dry test slide procedure, thus rendering it impractical for rapid screening tests. In the original latex fixation test described by Singer and Plotz the latex and gamma globulin reactants are made only when needed for immediate testing. Finally, a similar problem has been noted in commercial liquid preparations of latex fixations tests, the sensitivity of which shifts over time.

It is an object of this invention to overcome these disadvantages of the SCAT test (and also the disadvantages of the latex fixation tests) by providing a test as specific as the SCAT but having a sensitivity comparable to that of the FII latex fixation test.

It is also an object of this invention to eliminate the necessity of using red cells, which do not have a long shelf life.

It is also an object of this invention to provide a test which may be embodied as a dry test slide for rapid screening and recording of test results.

It is also an object of this invention to provide a test which may be performed easily and which retains its sensitivity over time.

SUMMARY OF THE INVENTION

The invention is based on the discovery that red cell stroma may be employed for coating with globulins. Stroma, or stromata, is the spongy protoplasmic framework (reticulum) of a cell, particularly a blood cell.

More particularly the invention is based on the discovery that sheep red cell stroma may be coated with rabbit anti-sheep cell gamma globulin. Globulins derived from human or equine sources may also be used.

In the preferred embodiment of the invention sheep red cell stroma are coated with a subagglutinating amount of rabbit anti-sheep cell serum or globulin. These sensitized stroma are useful as a means for detecting RF by an agglutination reaction similar to that for the sensitized red cells themselves. The sensitized red cell stroma is preferably used with an absorbing antigen to prevent interference by heterophile antibodies. In the case of sensitized sheep red cell stroma, the absorbing antigen is preferably comprised of guinea pig and beef antigens. The test using the sensitized stroma may be followed as a wet test-tube or wet test-slide procedure. The sensitized stroma may also be dried on a test slide for later reconstitution and use. The resulting agglutination products may themselves be dried on the test slide to make a permanent record of the test.

DESCRIPTION OF THE PREFERRED EMBODIMENTS

The reagent of the invention is a red cell stroma sensitized or coated with a globulin. Preferably, this reagent is used in association with an absorbing antigen. The reagent of the preferred embodiment of the invention is a sheep red cell stroma sensitized or coated with a rabbit anti-sheep gamma globulin. The associated absorbing antigen is comprised of guinea pig antigen and beef antigen. The preparation of the reagents of the invention and the absorbing antigen is as follows:

1. Preparation of Sensitized Red Cell Stroma

The preparation of stromas of red cells is well known to the art. A 1956 article by Jarsolow and Taliaferro describes lysis of red blood cells in buffered saline of decreasing tonicity followed by removal of hemoglobin by centrifugation. B. N. Jaroslow and W. H. Taliaferro, "The Restoration of Hemolysis Forming Capacity in X-Irradiated Rabbits by Tissue and Yeast Preparations", J. of Infect. Dis., 98:75 (1956). Preparation of red blood cell stromas is also described in U.S. Pat. No. 3,956,477 to Price, Prodell and Friedman and in U.S. Pat. No. 3,959,456 to Zichis.

In the case of sheep red cell stroma, a preferred preparation is as follows. Fresh sheep blood is obtained in an anticoagulant. Citrates are preferable as anticoagulants, but substitutes may be used such as sodium oxalate, potassium oxalate, ammonium oxalate, and heparin. A preferred citrate solution is Boerner-Lukens preparation. As described in O. Hepler, *Manual of Clinical Laboratory Methods,* 4th ed. (Thomas 1966) at page 222, it is composed as follows:

| Sodium citrate | 9.92 | gm. |
|---|---|---|
| Dextrose, anhydrous | 24.8 | gm. |
| Thimerosal | 0.1 | gm. |
| Distilled water q.s. | 100.0 | ml. |

It is used in the proportion of one part to nine parts blood. Another common citrate preparation is Alsever's Solution, which is composed as follows:

| Dextrose, anhydrous | 18.2 | gm. |
|---|---|---|
| Sodium citrate, dehydrated | 8.0 | gm. |
| Sodium chloride | 4.2 | gm. |
| Citric acid | 0.55 | gm. |
| Sodium azide | 2.0 | gm. |
| Distilled water q.s. | 1000.0 | ml. |

After collection, the platelets in the blood disintegrate. The collected blood is centrifuged at about 2000 rpm for 10 minutes whereupon a layer of white cells appear in the upper layer of the cell pack. This layer is carefully suctioned off together with the supernatant. The red cells which remain are then washed by suspending them in two or more volumes of a 0.9% (by weight) NaCl solution and centrifuging. Any additional white cell material noticed is removed as described. The wash steps are repeated as necessary to remove all white cell material. Washing is detailed further in Hepler, cited above. A preferred centrifuge for laboratory use both for washing and the other procedures to be described is the IEC Centrifuge Model HT High Speed Angle Head, available from the International Equipment Co., Needham, Mass. 02194. A centrifuge preferred for commercial preparation is the Beckman J-21 B available from Beckman Instruments, Palo Alto, Calif., or the IEC PR6000 available from International Equipment Co., Needham, Mass. 02194.

Washing of the sheep blood is performed to remove the plasma constituents and to free the surface of the cells of protein. By doing this the cell surface is exposed and the sensitization is easily achieved or if the sensitization is to occur after stroma formation, incubation of the washed cell allows for more rapid loss of the intracellular components.

After washing, the cells are resuspended by 4% by volume in borate buffer, borate buffer/saline or glycine solution of pH 6.4–8.2. An exemplary borate buffer solution is prepared by dissolving 30.0 gm. boric acid and 2.0 gm sodium azide in 1000 ml. of distilled water and then adding enough 5 N sodium hydroxide to bring the solution to pH 7.0. The purpose of the buffer is to allow the cell to form stroma slowly as the intracellular components leach out while at the same time maintaining the suspension relatively free of microbial contaminants, sodium azide being a bacteriocide. An exemplary borate buffer/saline solution is prepared by including 12 gm. of sodium chloride in the solute of the borate buffer solution just described. The inclusion of sodium chloride at this level allows for proper ionic characteristics for good stroma formation. An exemplary glycine buffer is: Glycine—7.5 gm; 1 N sodium hydroxide—2.5 ml.; Distilled water q.s. 1000 ml. The pH is adjusted to 8.2 with sodium hydroxide and 10 gm. of NaCl added. The buffers described in U.S. Pat. No. 3,956,477 could also be used. The determination of percent volume occupied by the cells can be determined by centrifuging a sample in a calibrated tube after which the cell pack volume can be easily determined.

After the washed cells are resuspended, the suspension is incubated. The rate of stroma formation is dependent upon the temperature at which the suspension is kept. Normally, the higher the temperature (up to the temperature where the proteinaceous material would denature or cook), the more rapid the stroma formation. A preferred temperature is 37° C., at which stroma formation occurs in about a week.

The incubation may take place in a stoppered glass or plastic bottle that is stored in the case of incubation at 2°–8° C. (the range permitted for refrigerated storage), in a walk-in refrigerator such as that available from Herema Co., Hawthorne, N.J., or in the case of 37° C. incubation, in a walk-in warm air incubator such as that available from Lab Line Instruments Inc., Melrose Park, Ill.

During the period of incubation, the suspension is mixed daily and after about three days, and then every day, samples are withdrawn. These samples are put in centrifuge tubes and centrifuged at a speed of 8000 rpm for about 30 minutes. The supernatant, which will be very darkly colored, is suctioned off using a Pasteur pipet fixed to a vacuum trap and line. The remaining material in the sample is resuspended to its initial volume in 0.9% sodium chloride solution and centrifuged under the same conditions. When stroma is forming it can be visualized as a tan flocculent layer, first appearing in the upper region. The cells which have not lost their integrity are denser and will appear as a very dark colored layer underneath. As stroma development occurs with time, more and more of the material will appear tan after the saline wash. Depending upon the "hardiness" of the original red blood cells, the amount of time required for stroma formation may vary but usually a week's incubation at 37° C. is sufficient. When lower temperatures are used, the incubation time is usually longer.

When the stroma has formed, it is centrifuged and the borate buffer removed. It is then washed by resuspension in 0.9% sodium chloride solution and centrifuged. The supernatant is carefully sucked off and the greyish layer appearing is the stroma and is removed and resuspended in saline. The dark bottom layer is discarded. The wash steps are then repeated for the stroma and at each centrifugation any dark layer noted is discarded. Washing is continued until the supernatant is clear, or light straw color, indicating it is free of hemoglobin, and the stroma is light beige or whitish in color.

After washing, the stroma is resuspended to 4% cell concentration, based on original volume in borate/saline buffer. Samples of the stroma suspension are titered against equal volumes of dilutions of the sensitizing agent, rabbit anti-sheep red cell serum, which contains gamma globulins. The dilutions begin with a 1:10 dilution from which two-fold dilutions are prepared, yielding dilutions of 1:10, 1:20, 1:40, 1:80, 1:160, 1:320, etc. All dilutions are prepared in saline or buffer solution of pH 6.4-8.2. Beginning with the most concentrated of the dilutions titering continues until a dilution is found which will not agglutinate the suspended stroma in the sample. The first dilution in which no agglutination is seen is the subagglutinating dilution. Then, to determine more exactly where agglutination fails to occur, a finer range of dilutions is selected beginning with the last dilution showing visible agglutination and these are tested. For example if the dilution 1:40 yields a ± reaction while 1:80 is negative, dilutions of 1:40, 1:50, 1:60, 1:70, 1:80 are prepared for testing. If dilutions greater than the subagglutinating dilution are used, the final test sensitivity will be affected. Gamma globulin should be used and the range selection is determined by the quality of the stroma and/or sensitizing agent.

2. Preparing the Stroma Reagent

An amount of the subagglutinating dilution of the rabbit anti-sheep red cell serum which is equal in volume to the amount of the stroma suspension to be sensitized is prepared and added to the stroma suspension. The mixture is then incubated at a temperature between 2°-56° C. to sensitize the stroma. Preferred incubation is at 37° C. in a walk-in air incubator for a period of several days. Sensitization is determined by withdrawing a sample and testing it for appropriate reaction against a panel of known RF positive and RF negative sera. It is also possible to sensitize the stroma during its formation as detailed in Example I.

After being sensitized, the stroma is washed in 0.9% NaCl solution to remove any sensitizing agent that has not been absorbed. It is then centrifuged at 8000 rpm and the supernatant discarded. The stroma is then resuspended in a buffer solution. The buffer solution preferably contains a dye for staining the sensitized stroma to enhance its visibility. A useful dye is Trypan Blue, obtainable from Matheson, Coleman and Bell, Norwood, Ohio. Other useful dyes include:

Evans Blue (Direct Blue 53)—Biological stain Matheson, Coleman and Bell, Norwood, Ohio
Bests Carmine Stain Compound, Paragon C. & C. Company, Inc., New York 58, N.Y.
Biebrich Scarlet (water soluble), Allied Chemical Company, National Aniline Division, New York, N.Y.
Thiazine Red R—Harleco (Hartman-Lordon Company), Philadelphia, Pa.
Neutral Red (Tolylene Red)—Matheson, Coleman and Bell, Norwood, Ohio, E. Rutherford, N.J.
Azocarmine G—Biological stain, Hartman-Lordon Company, Philadelphia, Pa.

The dye may be added earlier, but is preferably done at this stage to insure color intensity, since if added earlier a certain proportion of the dye will wash out resulting in lighter colored stroma.

It is also preferable that the buffer solution in which the sensitized stroma is suspended contain a bactericide to avoid or minimize the possibility of bacterial contamination. Suitable bactericides include:
Chloramphenicol
Sodium Penicillin
Neomycin Sulfate
Phenyl Mercuric Borate
Sodium Ethylmercurithiosalicylate
Thimerosal
Sodium Azide The last mentioned bacteriocide, sodium azide, while excellent in liquid preparation at about 0.1-0.2% should not be used in preparations where the reagents are to be dried by heating, since it will evolve dangerous hydrazoic acid. Thimerosal is best not used in liquid preparations of the claimed invention, since its effectiveness deteriorates over time in concentrated protein solution.

Finally, EDTA is preferably added to the suspension in a final concentration of 0.2%. It is a chelating agent and blocks complement present in fresh sera.

An example of a final suspension liquid for the stroma contains 3.0 gm. boric acid, 0.2 gm. sodium azide, 0.186 gm. EDTA (based on purity), 0.02 gm. Trypan blue, 1000.0 ml. distilled water q.s. The pH is adjusted to 7.0 with 5 N NaOH solution. On resuspension, at least a twenty-fold concentration of the stroma is made. For example, from an original volume of 11,200 ml. of a 4% cell suspension one would obtain 560 ml. of the final stroma suspension. Where the suspension is to be dried, the sodium azide would be omitted and 9% sucrose added.

3. Preparation of Absorbing Antigen

Where employed, the absorbing antigen is a mixture of guinea pig and beef stroma antigens prepared according to the following procedure:

a. Guinea Pig Antigen

Guinea pig antigen was prepared by placing a quantity of tissue of the kidney, lung, or spleen, from freshly sacrificed animals into a blender. When the tissue was finely ground and pooled, it was diluted with 0.9% saline to make an 18% (weight/volume) suspension. The suspension was allowed to stand at 2°-8° C. for two hours with occasional mixing. Subsequently, the suspension was centrifuged for 20 minutes at 4500 rpm. The supernatant was separated and heated rapidly to 56° C. in a water bath and maintained at this temperature for 30 minutes. Following heating, the material was stored at 2°-8° C. for about 24 hours. After 24 hours in the refrigerator, the material was centrifuged at 8000 rpm to clarify, and the clear supernatant was poured into a clean storage vessel for further use. Any precipitate was discarded.

b. Beef Antigen

Two gallons beef blood was collected in a 7.6% citrate solution at a slaughterhouse and immediately filtered through cotton gauze into an excess of Alsever's pH 6.1 solution. The resulting suspension was held under refrigeration for 7–10 days. The blood was then centrifuged and washed once in 0.9% sodium chloride solution. After centrifugation of the saline-cell mixture, the blood cells were resuspended in borate buffer (pH 7.0) and incubated at 25°0 C. until stroma developed. This can be determined by removing a sample and centrifuging it at 8000 rpm and examining the resultant layers that have precipitated. When a light brown flocculent layer is abundant, the material should be further processed by centrifuging at 8000 rpm. The supernatant was discarded and the resultant precipitate washed in 0.9% sodium chloride solution until the supernatant wash was light straw colored. At every centrifugation any dark tarry material remaining in the centrifuge bottles after resuspension of the lighter flocculent material was discarded. The final light colored precipitate was brought to a volume of 8 liters in a borate buffer (pH 7.0) that contained no sodium chloride.

c. Absorption Antigen

Equal volumes of the guinea pig antigen and beef antigen were mixed together and dilution of this material made in borate buffer pH 7.0 to make the absorption antigen composition, e.g., one part guinea pig antigen plus one part beef antigen plus two parts borate buffer. Before use, the absorption antigen is adjusted so that a high titer infectious mononucleosis (IM) serum is neutralized as determined by mixing rheumatoid factor serum with IM serum and testing for interference. IM serum possesses a high concentration of heterophilic antibodies, quite similar in reaction to the heterophilic antibodies which may be found in some RF sera. If not neutralized in the RF sera, these heterophilic antibodies can, if present in high enough concentration, cause non-specific agglutination of the stroma. To determine that neutralization has occurred, an RF serum of known titer is mixed with an equal amount of the IM serum mixture and a series of dilutions is prepared. The dilutions are mixed with an equal amount of the absorbing antigen and then with an equal amount of the stroma. The resulting mixtures are then observed to determine whether the reaction appropriate to the known RF titer is observed. If neutralization of the IM serum has been achieved with the absorption antigen, it may be assumed that the absorption antigen-preparation will also neutralize any heterophile antibodies which may be present in the RF test sera.

To test for specificity, a known negative RF serum is mixed with a known heterophile containing serum, such as IM serum, and the combination tested as above. There should be no agglutination observed.

General Test Procedure

The test of this invention may be used for whole blood, plasma, serum, or synovial fluid. The test fluids are obtained and prepared in the usual manner and although blood serum and synovial fluids are referred to below, the test method described is applicable to all test fluids.

In testing blood serum, it is extracted from clotted blood by gently breaking the clot that has formed and centrifuging the blood in the clotting tube. The serum will be amber colored and can be drawn off by Pasteur pipet or decanted so that blood cells are not carried along with the serum.

Synovial fluid is aspirated under sterile conditions from a joint. This material is usually similar to serum in consistency but may be particulate. In some cases, the synovial fluid may be thick and gelatinous. Should this be the case, an initial serial dilution should be made prior to testing.

It is not necessary to heat-inactivate the sample before use. The test sample should be serially diluted in 0.9% saline (1:1, 1:2, 1:4, 1:8 . . . ) if quantitation of RF is desired. In most instances this will be the case since the rise or fall in RF titer is often an index of the severity of the disease. A drop in titer (even to reversion to a negative test) with treatment, usually is indicative that the therapy is effective. A qualitative test on the other hand provides only information pertaining to the presence or absence of RF, and should not be considered diagnostic.

A wet slide test may be performed by placing, for example, 0.03 ml of absorbing antigen within a demarcated circle on a glass slide. 0.03 ml of the test sample or dilution is added, the two admixed, and the slide rocked to allow for the absorption of heterophile antibodies that might be present. This mixing should take about 30 seconds. A 0.03 ml. drop of the sensitized stroma is added and mixed with the combined reagents. In mixing, the reagents should spread evenly over the slide so that the entire circumscribed area is used. The slide is then slowly rocked, using a figure eight motion and observation made at about two minutes. The presence of agglutinates is considered a positive test; a homogeneous suspension is considered negative. When testing a series of dilutions the last dilution showing a discernible agglutination is taken as the end point and titer is reported as the reciprocal of the dilution.

Test Slides

A particularly advantageous embodiment of the invention is a test slide comprising a substantially planar strip of substrate material having at least one surface on which the test can be carried out. The sensitized stroma reagent of the invention is carried on the test surface in the form of a solid dried deposit. Where an absorbing antigen is employed, the test surface carries two separate deposits of dried reagents, one deposit being the sensitized stroma reagent and the other deposit being the absorbing antigen. The deposits are generally located in close proximity to each other and may if desired be positioned within a demarcated circumscribed test area.

The substrate material may, for example, be glass, glazed porcelain, or a synthetic material, e.g., a plastic material such as nitrocellulose or methyl methacrylate, or a phenol-formaldehyde resin, the surface of which has been treated so as to make it wettable, for example, by sand blasting or rubbing with an abrasive.

Preferably, the substrate is a thin sheet of cardboard having one or both surfaces coated with a coating of a water-impermeable and water-wettable coating of plasticized nitro cellulose, having a thickness which will maintain the flexibility of the cardboard, e.g., about 0.02 inch. In all cases, the surface of the substrate which carries the test reagent deposits should be water-soluble.

With reference to a test slide employing both the sensitized stroma reagent and an absorbing antigen, the deposited test reagents or spots advantageously have an average diameter between 5 and 10 mm., and are located in close proximity, in order that both may be admixed after being reconstituted to carry out the test. Preferably the slide is light in color, in order to provide a background against which the test results may be better observed.

In carrying out the test, the sample (about 0.03 ml) is first mixed thoroughly with the absorbing antigen, if used, for about thirty seconds. Then the sensitized stroma deposit is reconstituted to a homogeneous suspension with a measured amount (e.g., about 0.03 ml.) of distilled water. The reconstituted reagents are admixed thoroughly so that the surface of the circumscribed area is covered. The slide is then rocked in a figure-eight motion for two minutes, the motion being just sufficient to allow the mixture to flow across the card. At the end of this time, the mixture is observed for agglutination using a bright light source. The presence of rheumatoid factors is evidenced by agglutination. When testing dilutions of a sample, the dilution yielding the last agglutination is the end point and the titer is reported as its reciprocal.

To prepare suitable test slides, an approximate quantity (0.03 ml.) of a reagent is accurately measured onto a test slide. The reagent is then dried in dry air, heated at a temperature of about 45° C.

The manner in which quantities of reagents are applied to the slides or cards is immaterial except that the method must be accurate. For example, a suitable method is to employ a metering pump of suitable type, e.g., a Lambda pump, which is a solenoid-operated piston type pump, made of stainless steel, which will deliver from 0.01 cc. (10 Lambda) to 0.5 cc. per stroke, preferably 0.03 cc. Suitable pumps include those made by Harvard Apparatus, Mills, Mass. 02054 and Alphamedics Levittown, Pa. 19057, the latter being a preferred pump. The pressure of the issuing fluid is kept below a level which will cause splashing, for example, one drop per stroke, generally 10 strokes per second or less, depending on the rate of delivery desired.

Where two reagents are applied to the slide, they may be each dispensed as a single accurately measured drop side by side simultaneously. The substrate is then removed to a drier and the drops dried at 20° to 50° C., depending upon the heat resistance of the reagent. An optimal temperature is from 40° to 45° C. The dry slide can be used as such, or packaged in a moisture-proof protective container for storage.

In the preparation of the test slides or cards, the sensitized stroma reagent (and absorbing antigen where employed) is constituted as a solution or suspension in a volatile liquid medium, advantageously an aqueous medium. Such solutions or suspensions may also contain potentiating or resuspending aids. It has been found, in accordance with the invention that a number of adjuvants contribute to the ease of resuspension of dried reagents and serve to produce a firm bonding of the dried reagent to the test slide surface. These adjuvants include, for example, bovine serum albumin in concentrations up to and including 5% (wt./vol.), 1% being optimal; lactalbumin hydrolysate in concentrations up to and including 5%, 1% being optimal; and gum arabic in concentration of about 0.5%.

It has also been found, in accordance with the invention, that the inclusion of a saccharide in a 9% concentration in the reagent provides, upon drying, a hard, glaze-like finish to the dried test spot which protects it against abrasion and mechanical damage, thereby aiding in packing and storage. The saccharide also provides a matrix which helps to avoid disintegration of the reagent deposit. Sucrose and mannose are preferred saccharides, but any saccharide may be used if it possesses the proper drying qualities for matrix formation. This use of a saccharide is applicable to the dried test spot for the absorbing antigen, as well as that of the sensitized stroma.

There is an additional substance, PVP (polyvinylpyrrolidone), which may be added in a 0.1% concentration to the absorbing antigen where it is intended to be dried on a slide. It may also be used as in U.S. Pat. No. 3,956,477. The PVP acts as a potentiator. By reason of its molecular size, it facilitates agglutination.

EXAMPLE I

The purpose of this example is to examine the utility of sensitizing fresh sheep cells with various available antibodies after the cells had been prepared by collecting them fresh in citrate solution, washing them 2 times in 0.9% NaCl solution, and then resuspending to 4% cell concentration in either borate buffer or 0.9% NaCl solution. The cells were then processed in the following various ways:

1. In the first case, to 200 ml of sheep cells in saline was added 5.0 ml of FII gamma globulin solution (100 mg. % in 0.9% sodium chloride solution) that had been prepared and held frozen until ready for use. The cells were incubated in a glass container for 7 days at either 2°–8° in a refrigerator or 37° C. in a warm air incubator after which they were washed in 0.9% NaCl and resuspended to the original volume in borate buffer and then incubated in a glass container put into a warm air incubator at 37° C. until stroma formed.

2. In the second case, 100 ml of the cells prepared in saline were used and to them was added 100 ml. of a 1:37.5 dilution of rabbit anti-sheep serum preparation. Incubation and stroma formation were as in 1.

3. Equal portions of cells (100 ml. each) that had been mixed with either FII or rabbit anti-sheep serum 1:37.5 dilution were admixed and incubated as in 1.

4. To 100 ml. of sheep cells in saline was added 100 ml. of sheep cells in borate buffer. To this was added 5.0 ml. of FII stock solution and incubation conditions were as in 1.

5. To 100 ml. sheep cells in saline was added 100 ml. sheep cells in borate buffer and 100 ml. rabbit anti-sheep serum diluted in borate buffer (1:37.5 dilution). Incubation and stroma formation as in 1.

6. To 100 ml. sheep cells in borate/saline buffer containing 1.54 ml. rabbit anti-sheep serum diluted 1:65 was added 100 ml. sheep cells in borate/saline buffer containing 50 mg.% FII stock. Incubation as in 1.

7. To sheep cells in borate/saline buffer (100 ml.) was added 100 ml. FII stock solution (100 mg./100) and this combination was incubated at 2°–8° C. in a refrigerator throughout stroma formation.

8. To sheep cells in borate/saline buffer (100 ml.) was added 100 ml. rabbit anti-sheep serum (1:37.5 dilution) and this combination was incubated at 2°–8° C. in a refrigerator throughout stroma formation.

Testing of the above stroma with rheumatoid serum and serial dilutions (1:2-1:4-1:8-1:16-1:32 . . . ) was done by combining 0.03 ml. stroma with 0.03 ml. sample, mixing, rocking the mixture and then reading at about 2 minutes for agglutination. The tests confirmed reactivity (degree of agglutination) of the stroma especially in cases 1, 2, 3, 5, 7, and 8, as shown in the table below, where agglutination is based on the usual 0-4 scale.

|  | Stroma | 1 | 2 | 3 | 4 | 5 | 6 | 7 | 8 |
|---|---|---|---|---|---|---|---|---|---|
| Serum no. | 425 1:1 dil. | 4 | 2 | 1 | 0 | 4 | 1 | 0 | 4 |
|  | 2560 1:1 dil. | 2 | 4 | 4 | 0 | 4 | 0 | 4 | 4 |
|  | 2560 1:128 dil. | 0 | 4 | 4 | 0 | 4 | 0 | 4 | 4 |

Buffer Formulations Used:

A.
0.9% NaCl solution
9 gm. sodium chloride dissolved in 1 liter distilled water B.
Borate buffer s NaCl
Boric acid 30.0 gm.
5 N Sodium Hydroxide to pH 7.0
Sodium azide 2.0 gm.
Distilled water 1000 ml.

C.
Borate/Saline buffer
Boric acid 30 gm.
Sodium Chloride 12 gm.
Sodium azide 2.0 gm.
5 N Sodium Hydroxide to pH 7.0
Distilled water 1000 ml.

EXAMPLE II

The purpose of this example is the determination of preferred stroma preparation, buffering system and pH.

Sheep stroma coated with a subagglutinating amount of rabbit anti-sheep serum were suspended in various buffers including a borate/saline or glycine buffer to a 20-fold concentration of the volume used in sensitizing. Dilutions of the patient specimens were also prepared in various buffers (glycine, borate, or 0.9% sodium chloride solution) for testing. The stromas had been prepared by incubation with the sensitizing solution at 37° C. for a week, dyed using trypan blue, and EDTA added. Guinea pig and beef antigens were used as neutralizing antigens for any possible heterophile antibodies in the patient specimens prior to mixture of the test samples with the stroma. The readings in the table are based on a scale of 4+ for maximum agglutination and 0 for no visible agglutination macroscopically.

| Specimen dil. | 1:2 | 1:4 | 1:8 | 1:16 | 1:32 | 1:64 |
|---|---|---|---|---|---|---|
| Stroma + Borate, EDTA | 3+ | 2+ | 1+ | 1+ | 1+ | 1+ |
| Stroma + Glycine, EDTA | 3+ | 1+ | 1+ | 1+ | 1+ | 1+ |
| Stroma + Saline | 2+ | 2+ | 1+ | 0 | 0 | 0 |
| Stroma + Borate | 2+ | 1+ | 1+ |  |  |  |

EXAMPLE III

Dried test reagents were prepared by adding sucrose (9%) to liquid suspensions of stroma and absorbing antigen, placing known quantities (0.03 ml) on a paper test slide and submitting them to heat (40°-65° C.) sufficiently long to dry them.

Subsequently the test slides were used in a clinical evaluation of laboratory samples that yielded excellent correlation with patient status.

Examples of reactions that occurred included:

| Sample | Latex Tests A | B | Stroma | SHC[1] | SSCT[2] Waaler Rose |
|---|---|---|---|---|---|
| 1 | + | + | + | 320 | 80 |
| 2 | − | − | − | − | − |
| 3 | + | + | + | 1280 | 320 |
| 4 | + | ± | − | 80 | − |
| 5 | + | + | − | − | − |
| 6 | + | + | + | 640 | 160 |
| 7 | + | + | + | 640 | 160 |
| 8 | − | − | − | − | − |
| 9 | − | − | − | − | − |
| 10 | − | − | − | − | − |
| 11 | − | − | − | − | − |
| 12 | + | + | + | 640 | 80 |
| 13 | + | + | − | 40 | − |
| 14 | − | − | − | − | − |
| 15 | − | − | − | − | − |
| 16 | + | + | + | 1280 | 320 |
| 17 | − | − | + | − | − |

[1]Results considered comparable to tube latex test
[2]Sheep cells sensitized at 1/20 B.A.T.

The sensitized latex and stroma tests are reported as + or − for agglutination and non-agglutination, respectively. SHC tests are based on sensitized human cells and are reported as titer of sample. SSCT tests (Waaler-Rose) are the usual SCAT tests.

EXAMPLE IV

Quantitative testing of sera from individual diagnosed as having rheumatoid arthritis.

| Example: | | Serial Dilutions in 0.9% Saline | | | | | | | |
|---|---|---|---|---|---|---|---|---|---|
| | | 1:1 | 1:2 | 1:4 | 1:8 | 1:16 | 1:32 | 1:64 | 1:128 |
| Samples collected | 2/19 | 4 | 4 | 4 | 4 | 4 | 4 | 2 | 1 |
| | 2/22 | 4 | 4 | 4 | 4 | 4 | 3 | 1 | ± |
| | 3/6 | 4 | 4 | 4 | 4 | 4 | 2 | 1 | Neg. |

In the above example, patient sera obtained during treatment were tested. Dilutions of the sera were made in 0.9% sodium chloride solution and tested with stroma that had been sensitized. In testing, a 0.03 ml amount of serum or dilution was mixed with 0.3 ml of stroma, the test slides rocked for two minutes and the degree of agglutination obtained with each dilution recorded. Agglutination patterns range from maximal (4±) to minimal (barely visible: ±).

What is claimed:

1. A reagent for the detection of rheumatoid factors in human blood, plasma, serum or synovial fluid by immunochemical reaction with the factors, consisting essentially of a supply of red cell stroma having adsorbed upon their surface a sensitizing agent, which sensitizing agent sensitizes the red cell stroma for the detection of said rheumatoid factors.

2. The reagent of claim 1 wherein the red cell stroma is sheep red cell stroma.

3. The reagent of claim 2 wherein the sensitizing agent is a globulin.

4. The reagent of claim 2 wherein the sensitizing agent is rabbit anti-sheep red cell globulin.

5. The reagent of claim 2 wherein the sensitizing agent is human FII gamma globulin.

6. A test slide adapted for the performance on the surface thereof of an immunochemical test for detection of rheumatoid factors in human blood, plasma, serum or synovial fluid, comprising:

a substantially planar strip of substrate material having at least one test surface whereon is positioned (1) a deposit of solid dried red cell stroma, said stroma having adsorbed upon their surface a sensitizing agent, which sensitizing agent sensitizes the red cell stroma for the detection of said rheumatoid factors, (2) a second dried deposit of absorbing antigen capable of combining with heterophile antibodies in said blood, plasma, serum or synovial fluid, said test deposits being positioned in close proximity on said test surfaces.

7. The test slide of claim 6 wherein the test surface carries a demarcated test area wherein said dried deposits are situated.

8. The test slide of claim 6 wherein the substrate material is a substantially rectangular sheet of cardboard carrying on one surface a coating of a water-impermeable and water-wettable synthetic material.

9. The test slide of claim 8 wherein the synthetic material is a thin layer of plasticized nitrocellulose.

10. The test slide of claim 6 wherein the deposit of absorbing antigen includes both guinea pig and beef stroma antigens.

11. The test slide of claim 6 wherein the red cell stroma is sheep red cell stroma.

12. The test slide of claim 11 wherein the sensitizing agent is a globulin.

13. The test slide of claim 6 wherein the sensitizing agent is rabbit anti-sheep red cell globulin.

14. The test slide of claim 6 wherein the sensitizing agent is human FII gamma globulin.

15. A method for preparing sensitized red cell stroma, the resulting sensitized stroma providing a reagent for detecting rheumatoid factors in human blood, plasma, serum or synovial fluid by immunochemical agglutination, said method comprising the steps of:

(a) preparing an aqueous suspension of red cell stroma;

(b) mixing said suspension with a solution of a sensitizing agent, which sensitizing agent sensitizes the red cell stroma for the detection of said rheumatoid factors; and (c) incubating said mixture to adsorb the sensitizing agent to the cell stroma;

(d) washing said incubated mixture and sensitized cell stroma therein to remove any unadsorbed sensitizing agent; and (e) resuspending the washed incubated stroma in a buffered dye solution to impart a color to the stroma.

16. The method of claim 15 wherein the red cell stroma is sheep red cell stroma.

17. The method of claim 16 wherein the sensitizing agent is a globulin.

18. The method of claim 16 wherein the sensitizing agent is rabbit anti-sheep red cell globulin.

19. The method of claim 6 wherein the sensitizing agent is human FII gamma globulin.

20. The method for detection or determination of rheumatoid factors in human blood, plasma, serum or synovial fluid by means of the immunochemical reaction of said factors, which method comprises:

(1) admixing a predetermined amount of a neat or serially diluted sample of said blood, plasma, serum or fluid with a predetermined amount of an absorbing antigen capable of combining with heterophile antibodies in said blood, plasma, serum or synovial fluid;

(2) further admixing with mixture (1) a predetermined amount of a reagent having as its essential reactive component a supply of red cell stroma coated with a sensitizing agent, which sensitizing agent sensitizes red cell stroma for the detection or determination of said rheumatoid factors; and (3) detecting or determining the presence or extent of agglutination of the rheumatoid factors with said sensitized reagent (2), which detection or determination is a measure of the presence or quantity of said rheumatoid factors in said sample.

21. The method of claim 20 wherein the red cell stroma is sheep red cell stroma.

22. The method of claim 20 wherein the sensitizing agent is a globulin.

23. The method of claim 22 wherein the sensitizing agent is rabbit anti-sheep red cell globulin.

24. The method of claim 22 wherein the sensitizing agent is human FII gamma globulin.

* * * * *